United States Patent
Taylor et al.

(10) Patent No.: US 8,827,968 B2
(45) Date of Patent: Sep. 9, 2014

(54) TISSUE SPECIMEN RETRIEVAL BAG, METHOD FOR RETRIEVING TISSUE

(75) Inventors: James Taylor, Bartlett, IL (US); Robert H. Thrun, Bloomingdale, IL (US)

(73) Assignee: Anchor Products Company, Addison, IL (US)

( * ) Notice: Subject to any disclaimer, the term of this patent is extended or adjusted under 35 U.S.C. 154(b) by 660 days.

(21) Appl. No.: 12/797,862

(22) Filed: Jun. 10, 2010

(65) Prior Publication Data

US 2010/0318045 A1    Dec. 16, 2010

Related U.S. Application Data

(60) Provisional application No. 61/185,821, filed on Jun. 10, 2009.

(51) Int. Cl.
*A61M 1/00* (2006.01)
*A61B 17/00* (2006.01)

(52) U.S. Cl.
CPC . *A61B 17/00234* (2013.01); *A61B 2017/00287* (2013.01)
USPC .......................................... 604/317; 604/540

(58) Field of Classification Search
USPC .......... 604/317, 540, 172; 606/114, 113, 127, 606/128, 200; 600/37, 573, 580; 221/33
See application file for complete search history.

(56) References Cited

U.S. PATENT DOCUMENTS

| | | | |
|---|---|---|---|
| 6,409,733 B1 * | 6/2002 | Conlon et al. | 606/114 |
| 2004/0116828 A1 * | 6/2004 | White, Jr. | 600/573 |
| 2008/0045994 A1 * | 2/2008 | Rehnke | 606/190 |

* cited by examiner

*Primary Examiner* — Tatyana Zalukaeva
*Assistant Examiner* — Benedict L Hanrahan
(74) *Attorney, Agent, or Firm* — Cherskov Flaynik & Gurda LLC

(57) ABSTRACT

A tissue retrieval bag is provided, comprising a region of the bag defining an opening; a pleated fold intersecting said opening at a distal region of the opening; and a hem circumferentially formed around said opening, the hem forming insertion points adapted to receive a draw string, the insertion points in direct opposition to the pleated fold.

13 Claims, 4 Drawing Sheets

TISSUE SPECIMEN RETRIEVAL BAG, METHOD FOR RETRIEVING TISSUE

PRIORITY CLAIM

This utility application claims the benefit of U.S. provisional application 61/185,821 filed Jun. 10, 2009.

BACKGROUND OF THE INVENTION

1. Field of the Invention.

This invention relates to a tissue specimen bag and a method for retrieving tissue, and more particularly this invention relates to a folded bag and to a method for deploying the fold while the bag is inside a patient.

2. Background of the Invention.

Surgery of the past involved large incisions (typically greater than 10 centimeters in length) to access interior regions of the body.

In an effort to minimize scarring, infection, pain and other trauma, laparoscopic surgery has been developed. This surgery utilizes a laparoscope, a video camera with a lamp and surgical instruments inserted through small incisions (typically less than 3 centimeters) to better effect surgical repair. The incisions are typically fortified with grommet like devices called trocars so that no trauma to the skin occurs as instruments, sutures, and the like are passed through the incisions.

Surgery also is performed utilizing the body's natural portals. Recently, stomach surgery has been devised whereby the abdomen and other organs are accessed solely from the patient's mouth, umbilicus and other natural portals.

Whether performed the old fashioned way, or through laparoscopy, or just utilizing the body's natural portals, virtually all surgeries end up producing tissue waste. Tissue harvesting devices exist for gathering and removing such waste from inside a patient.

Many tissue retrieval devices feature bags positioned at the distal end of the device. These bags invariably remain attached to the device. One such device is taught in U.S. patent application Ser. No. 12/079,172, filed on Mar. 24, 2008, and incorporated herein by reference. This device comprises a bag which reversibly deploys at the end of an introducer tube. It is designed for use in laparoscopic surgeries.

A need exists in the art for a tissue retrieval bag which is not associated with a particular surgery modality, or with particular surgical instruments. The bag must be easy to deploy with a minimum number of instruments. A need also exists for a method for harvesting tissue from a patient with minimum effort and hardware.

SUMMARY OF INVENTION

An object of this invention is to provide a tissue retrieval bag and a method for harvesting tissue that overcome many of the drawbacks of the prior art.

Another object of this invention is to provide a stand alone tissue retrieval bag. A feature of this invention is a fold confined to one region of an opening to the bag. An advantage of this invention is that the fold provides a means for actuating the bag with a single motion by the user.

Still another object of this invention is to provide a method for harvesting tissue. A feature of this invention is that the mouth of a specimen bag used in the method is reversibly deployed and collapsed at a single point while a second point of the mouth is held stationary by the user. An advantage of the method is that a maximum of two instruments are required to deploy the bag, collect tissue, undeploy the bag, and remove the bag from the patient.

Yet another object of this invention is to provide a tissue specimen bag for use in a myriad of different surgery modalities. A feature of the bag is a lowermost surface adapted to receive a gripping tool and an uppermost means for actuating closure of the mouth of the bag. An advantage of the invention is its adaption for use in typical surgeries, laparoscopic surgeries, or surgeries involving ingress and egress via natural portals.

Briefly, the invention provides a tissue retrieval bag comprising a region of the bag defining an opening; a pleated fold intersecting said opening; and a hem circumferentially formed around said opening, said hem forming apertures adapted to receive a drawstring.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

The foregoing summary, as well as the following detailed description of certain embodiments of the present invention, will be better understood when read in conjunction with the appended drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a tissue retrieval device and a method for retrieving tissue. An embodiment of the device includes a reversibly deformable bag having an open first end and a closed second end. In close spatial relation to the second closed end is a region adapted to receive a grabbing tool, such tool being forceps, a tweezers, or some other surgical instrument. An exemplary feature of the invention is a pleat fold along one longitudinally extending region of the bag.

Figure 1:
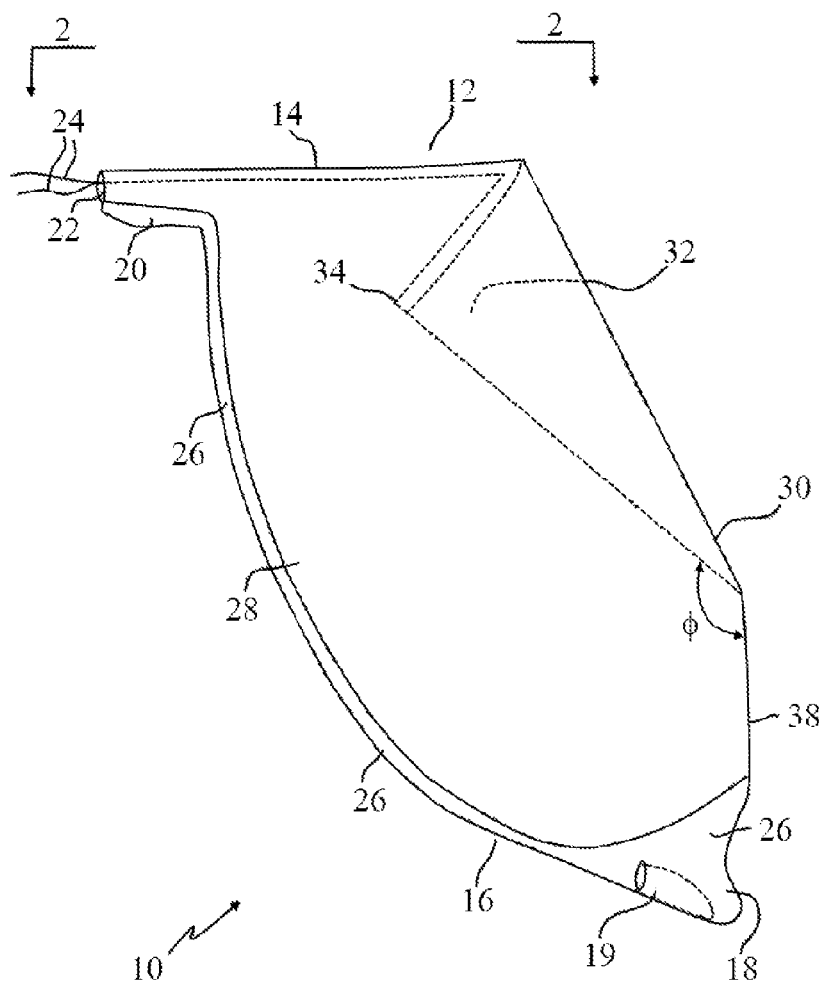
FIG. 1 is an elevational view of the invented bag in an undeployed configuration, in accordance with features of the invention.

FIG. 1 provides an elevational view of an embodiment of the bag, designated as numeral 10, in an undeployed configuration. A first end 12 of the bag defines an opening 14. A second end 16 of the bag 10 in close spatial relationship to the depending proximal edge of the bag) defines a first engagement point 18 adapted to receive a grabbing (i.e, pulling) tool or a else a pushing tool. The embodiment shown has this engagement point at the bottom-most portion of the bag. This tool engagement position eliminates bunching of the bag while the tool is used to pull or push the bag through a narrow passageway. A second engagement point 20 is situated at a region proximal to the opening 14. Superior to the second engagement point is a hem defining a channel 22 which circumscribes the opening. The channel is adapted to receive a drawstring 24.

The grabbing tool engagement regions 18 and 20 are situated at opposite ends of a contiguous, heat welded (or alternatively stitched and sealed) portion 26 of the bag. This heat welded portion 26 extends along substantially one entire longitudinal side of the bag, and in the embodiment shown, along the proximal longitudinal side 28 of the bag. The effect of heat welding is a thickening of the bag substrate at the point of the weld. This confers a more stout, tear resistant foundation for the region designated for engagement with the grabbing implement.

Another means for facilitating grabbing of the bag are one or more button holes (not shown), similar to grommets, formed in the first and/or second engagement regions.

Along a distal, longitudinal side 30 of the bag is formed a pleat 32, depicted in phantom in FIG. 1.

Figure 2:
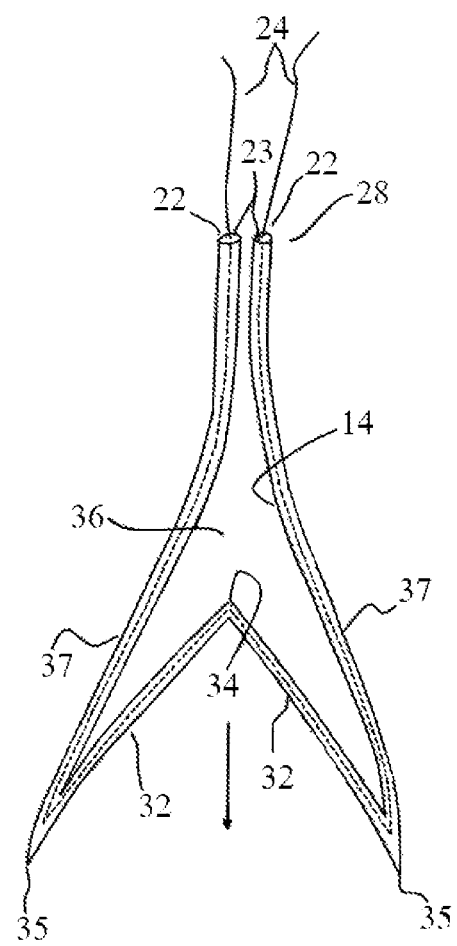
FIG. 2 is a view of FIG. 1 taken along line 2-2.

FIG. 2 provides a view of FIG. 1 taken along lines 2-2 of FIG. 1. FIG. 2 more clearly shows the opening 14 in the bag. Circumscribing the opening 14 is the channel 23, adapted to receive the drawstring 24 depicted partially in phantom.

Also shown in FIG. 2 is the pleat 32 in its undeployed configuration. In this embodiment of the invention, the pleat is undeployed such that its apex 34 is directed medially, or inwardly toward the proximal longitudinal side 28 of the bag. Deployment of the bag occurs when the user applies a force on the apex 34 in a lateral or distal direction so as to urge or otherwise force the apex in a direction away from the proximal longitudinal side 28 and toward the distal longitudinal side 30 of the bag. One method for deploying the pleat 32 includes physically grabbing the pleat at its apex 34 and pulling in a distal direction while holding the second engagement point 20.

Another method for deploying the pleat is to nest or otherwise insert a probe, hemostat, or other tool in the cavity 36 formed by the bag and applying a lateral force (in the direction of the arrow in FIG. 2) to the interior surface of the distal longitudinal side of the bag until the pleat snaps to a deployed configuration.

Pleat Positioning Detail

A salient feature of the invention is the positioning of the pleat 32 such that its apex 34 opposes the second engagement point 20 of the bag. Optionally, and as shown in FIG. 2, the pleat 32 is situated in opposition to the insertion point 23 of the draw strings in the channel 22. The pleat comprises the apex 34 and two flanking apexes 35. Together, the pleat may comprise up to half of the opening of the bag, but a range of arcs between one fifth and one third of the opening of the bag is preferred.

Preferably, the central apex 34 of the pleat directly opposes the proximal lip of the bag opening 14 which is in close spatial relationship to the second engagement region 20 and/or the drawstring insertion point 33. The proximal lip of the bag opening is so referred inasmuch as the bag is held or otherwise manipulated via the second engagement region 20 during pleat deployment.

Generally, the pleat extends down along about three fourths of the distal longitudinal side 30 of the bag. The remaining fourth 38 of the distal longitudinal side depends from the undeployed pleat at an obtuse angle θ and terminates at a region of the bag defining the aforementioned heat weld 26. In one embodiment, however, the pleat extends from the mouth of the bag to its bottom.

Figure 4:
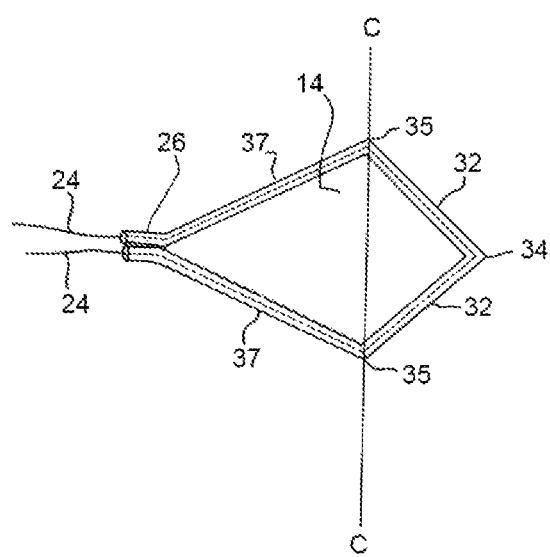
FIG. 4 is a view of FIG. 3C taken along line 4-4.

The aforementioned pleat positioning allows for maximum leverage to the user in definitively deploying and collapsing the bag. Once the pleat is deployed, as depicted in FIG. 4, the user can actuate the draw string to close the bag once it is full. Alternatively, opening 14 of the bag can occur via drawstring actuation while the pleat is not deployed.

Configurations of the pleats can vary. Depicted in FIG. 2 is a "W-shape pleat" i.e. a box pleat whereby two planarly shaped exterior regions 37 of the bag straddle a crease (defined by the apex 34) forming a superior region of the distal longitudinal edge of the bag. The two planar exterior regions form two exterior sides of the bag facing in opposite directions and coplanar to each other. Intermediate the aforementioned sides are positioned two panels 32, integrally molded with the exterior regions 37 so as to hingeably communicate with the exterior regions via a crease defined by the flanking apexes 35. These two panels 32 face each other. These two panels 32 are substantially equal in size and formed when the sides 37 are folded at the points (apexes 35) of intersection of the chord line "C" with the bag periphery defining the border of the pleat. The chord line "C" is depicted in FIG. 4.

This box pleat confers rigidity to the panels such that the pleat springs open to reveal the full periphery of the mouth when the panels are urged to do so, as described infra.

Operation Detail

The bag can be used in any tissue harvesting situation. In laparoscopic situations, the bag provides a unique harvesting method as follows:

As described supra, laparoscopic surgeries require the establishment of a plurality of small incisions. These incisions are generally kept intact with the use of a trocar. The invented bag is utilized in these situations, and with trocars having diameters as small as 5 millimeters (mm). Typical trocar diameters range from about 3 to 20 mm. Construction materials comprising the bag allow for the bag to be folded and otherwise compacted for passage through the trocar. These construction materials are similar to those used for the bag described in U.S. patent application Ser. No. 12/079,172, heretofore incorporated by reference. These materials confer a certain "memory" to the structure of the bag such that deployment will overcome the memory and define a diamond-shaped cross section suitable for easier tissue placement in the retrieval bag. The diamond configuration is depicted in FIG. 4. Other cross section shapes for the open mouth of the bag are also suitable. However, the diamond shape mouth opening combined with the memory function of the bag constituent, keeps the bag opening 14 propped open during harvesting operations.

Figure 3:
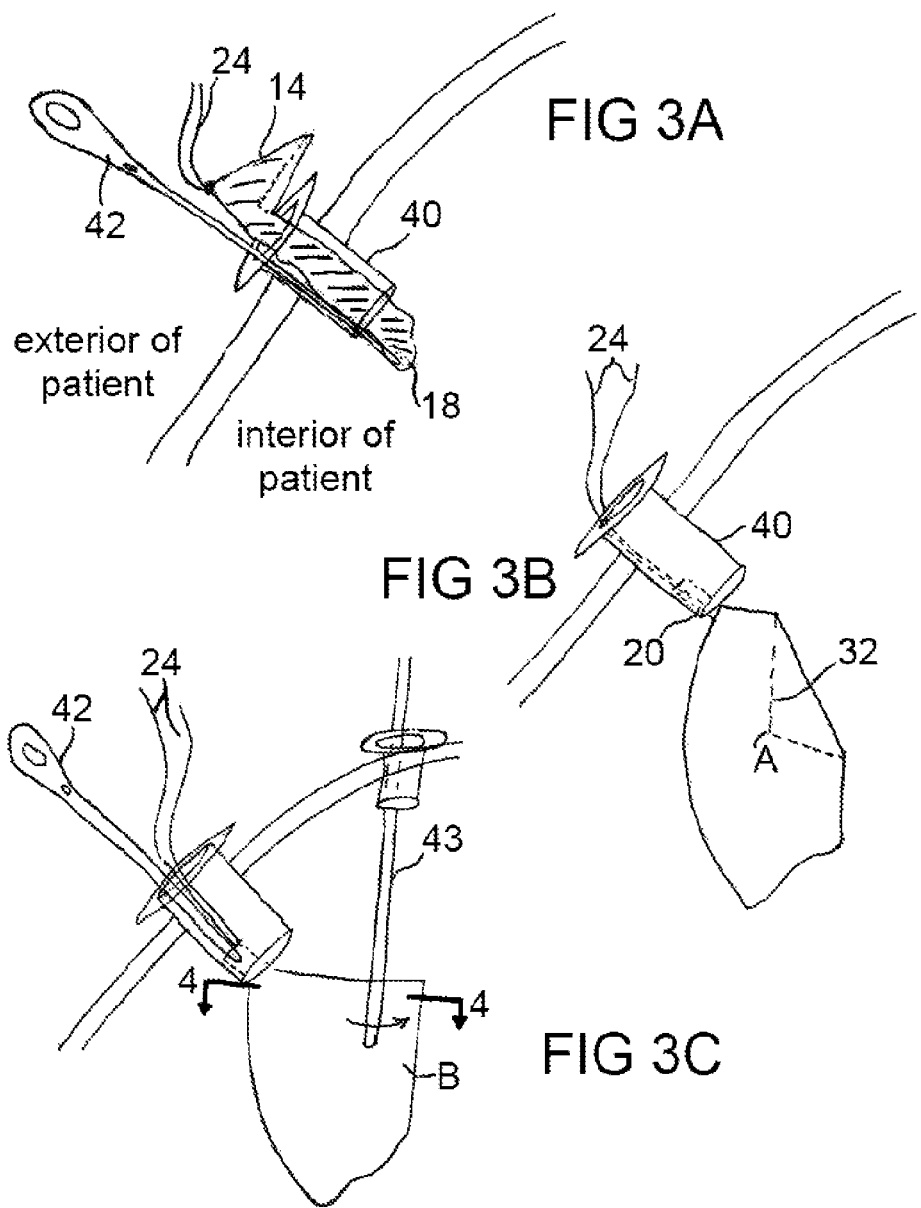
FIG. 3A-C are schematic diagrams of the invented method, in accordance with features of the present invention.

Prior to the bag being introduced into a trocar 40, forceps, tweezers, or other grabbing means 42 are removably attached to the first engagement point 18 at the lower most portion of the exterior of the bag adapted to receive the grabbing means. Instead of the first engagement point defining a region for grabbing by forceps, or hemostats, the first engagement point can define a pocket, 19, partially shown in phantom, adapted to receive a simple blunt-ended probe. As depicted in FIG. 3A, the user stabilizes the trocar 40 with one hand and with the other hand feeds the bag into the trocar, using the grabbing means 42 or probe.

Once the bag is passed through the trocar, the user releases the first engagement point 18 and withdraws the grabbing means from the trocar. As depicted in FIG. 3B, the drawstring remains extending out of the trocar to be manipulated by the user. Also depicted in FIG. 3B is the bag positioned such that the second engagement point 20 is accessible via the first trocar 40 so that the forceps 42 can engage that second engagement point 20.

Because of the pleated fold and of the afore-mentioned memory in the material of the bag, once unfolded, the bag tends to remain open without requiring that the surgeon use a tool to keep it open.

A second surgical instrument 43 such as a probe, forceps, suction tube or other elongated structure accesses the bag in the patient via a second trocar so as to provide a means to deploy the pleat of the bag by applying a distally extending force (see arrow) to the interior of the distal longitudinal side 30 of the bag. Upon full deployment of the pleat (see "B" in FIG. 3C), the memory characteristics conferred to the bag facilitate full access to the interior of the bag. At this point, the bag is ready to be filled with tissue.

The fully deployed pleat, thereby providing access to the full mouth of the bag, is shown in FIG. 4.

After the bag is filled, the bag pleat can be renested using the second probe, or else the bag, in the fully deployed configuration can be closed via the drawstring. In the case of re-nesting the box pleat, the second instrument 43 urges the mouth of the bag closed by applying a medial force to the outside surface of the distal longitudinal side of the bag.

As noted supra, typically a camera and a lamp are also inserted near the surgical site to allow the surgeon to monitor the progress of the operation. In an exemplary embodiment of this invention, regions of the bag and of the drawstring are impregnated with one or more luminescent materials such that the drawstring and these regions emit light of characteristic colors when illuminated by said light. Said regions of the bag may include, but are not limited to, the hem channel 23, the engagement points 18 and 20, and the longitudinal side 28.

It is to be understood that the above description is intended to be illustrative, and not restrictive. For example, the above-described embodiments (and/or aspects thereof) may be used in combination with each other. In addition many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and " in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The invention claimed is:

1. A stand alone tissue retrieval bag for direct insertion in a patient's body through a trocar, said bag comprising:
   a) a region of the bag comprising an opening;
   b) a pleated fold intersecting said opening;
   c) a hem circumferentially formed around said opening, said hem forming insertion points adapted to receive a draw string;
   d) a material possessing shape-preserving memory so that the bag opening assumes a pre-determined configuration after the bag is introduced unfolded in a patient's body;
   e) a first grabbing tool engagement region along a heat-welded portion of the bag extending along a longitudinal side of the bag forming a pleat wherein said pleat is used to deploy the bag and upon deployment said shape-preserving memory sections facilitate full access to the interior of the bag;
   f) the opening is on a first end of the bag, and a second grabbing tool engagement region is located on the second end of the bag; and
   g) a performed pocket is configured on an outside portion of the bag on the second end of the bag, and the pocket comprises a longitudinally extending region, with a portion of that longitudinally extending region reinforced so as to receive a blunt probe.

2. The bag as recited in claim 1 wherein the fold is restricted to a distal-most region of said opening.

3. The bag as recited in claim 1 wherein the fold is restricted to a part of the opening opposite the insertion points.

4. The bag as recited in claim 1 wherein the bag opening remains open once the bag is unfolded.

5. The bag as recited in claim 1 wherein the opening has a diamond-shaped cross section.

6. The bag as recited in claim 1 wherein the fold is deployed from a medially directed to a laterally directed configuration by pulling on the draw strings.

7. The bag as recited in claim 6 wherein the opening may be closed by pulling on the draw-strings when the fold is in a medially directed configuration.

8. The bag as recited in claim 6 wherein the opening may be closed by pulling on the draw-strings when the fold is in a laterally directed configuration.

9. The bag as recited in claim 1 wherein the bag comprises luminescent regions that emit light when illuminated by a light inserted in the patient.

10. The stand alone tissue retrieval bag recited in claim 1 wherein the bag is dimensioned so that it may be inserted in trocars between 5 and 20 mm diameter.

11. The stand alone tissue retrieval bag recited in claim 1 wherein said draw string insertion points are proximal to the first grabbing tool engagement region.

12. The stand alone tissue retrieval bag recited in claim 1 wherein the bag pleat comprises a W-shape pleat.

13. The bag as recited in claim 1 wherein the bag may be closed by pulling on the draw-strings.

* * * * *